US008809446B2

(12) United States Patent
Maddox et al.

(10) Patent No.: US 8,809,446 B2
(45) Date of Patent: *Aug. 19, 2014

(54) SUBSTITUTED 3-OXOPENTANOATES AND THEIR USES IN COATING COMPOSITIONS

(75) Inventors: John Thorton Maddox, Jonesborough, TN (US); Robert Lee Eagan, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 634 days.

This patent is subject to a terminal disclaimer.

(21) Appl. No.: 12/968,780

(22) Filed: Dec. 15, 2010

(65) Prior Publication Data

US 2012/0157609 A1  Jun. 21, 2012

(51) Int. Cl.
C07C 69/716 (2006.01)
C09D 5/02 (2006.01)
C08F 220/14 (2006.01)
C08F 220/28 (2006.01)

(52) U.S. Cl.
CPC .............. C07C 69/716 (2013.01); C09D 5/024 (2013.01); C08F 220/14 (2013.01); C08F 2220/283 (2013.01); C08F 2220/282 (2013.01)
USPC ........... 524/558; 524/559; 524/560; 524/561; 524/562; 526/309; 526/321; 526/322; 526/323; 526/323.1; 526/323.2; 560/174

(58) Field of Classification Search
CPC ... C07C 69/716; C08F 220/06; C08F 220/14; C08F 2220/282; C08F 2220/283; C08F 2220/1825; C09D 5/024
USPC .......... 524/558, 559, 560, 561, 562; 526/309, 526/321, 322, 323, 323.1, 323.2; 560/174
See application file for complete search history.

(56) References Cited

U.S. PATENT DOCUMENTS

| 3,197,500 A | 7/1965 | Kitchens et al. |
| 3,214,461 A | 10/1965 | Elam et al. |
| 3,220,865 A | 11/1965 | Coney |
| 3,892,903 A | 7/1975 | Dowbenko |
| 4,215,195 A | 7/1980 | Ponticello et al. |
| 4,839,413 A | 6/1989 | Kiehlbauch et al. |
| 4,855,349 A | 8/1989 | Ingle |
| 4,927,876 A | 5/1990 | Coogan et al. |
| 4,939,233 A | 7/1990 | Jenkins et al. |
| 4,946,932 A | 8/1990 | Jenkins |
| 5,055,506 A | 10/1991 | Knutson |
| 5,073,445 A | 12/1991 | Ingle |
| 5,137,961 A | 8/1992 | Goos et al. |
| 5,155,252 A * | 10/1992 | Yamamoto et al. ............ 560/190 |
| 5,247,040 A | 9/1993 | Amick et al. |
| 5,296,530 A | 3/1994 | Bors et al. |
| 5,349,026 A | 9/1994 | Emmoms et al. |
| 5,391,624 A | 2/1995 | Rasoul et al. |
| 5,484,849 A | 1/1996 | Bors et al. |
| 5,494,975 A | 2/1996 | Lovoie et al. |
| 5,498,659 A | 3/1996 | Esser |
| 5,519,071 A * | 5/1996 | Rheinberger et al. ......... 523/116 |
| 5,534,310 A | 7/1996 | Rokowski et al. |
| 5,539,073 A | 7/1996 | Taylor et al. |
| 5,721,329 A | 2/1998 | Fujiwa et al. |
| 5,756,826 A | 5/1998 | Hanselmann |
| 5,820,993 A | 10/1998 | Schall et al. |
| 5,872,297 A | 2/1999 | Trumbo |
| 5,886,116 A | 3/1999 | Trumbo |
| 5,889,098 A | 3/1999 | Trumbo |
| 5,932,350 A | 8/1999 | Lauer et al. |
| 5,945,489 A | 8/1999 | Moy et al. |
| 5,962,556 A | 10/1999 | Taylor |

(Continued)

FOREIGN PATENT DOCUMENTS

EP  0 241 127 A2  10/1987
EP  0 492 847 A2  7/1992

(Continued)

OTHER PUBLICATIONS

Moszner, Norbert et al., Reaction behavior of β-ketoesters: 3. Polymerizable reaction products of 2-acetoacetoxyethyl methacrylate with aromatic isocyanates and aldehydes, Polymer Bulletin 33, (1994), 43-49.

(Continued)

*Primary Examiner* — Peter D Mulcahy
(74) *Attorney, Agent, or Firm* — James K. Leonard

(57) ABSTRACT

Substituted 3-oxopentanoates are disclosed that correspond to the following formula 1:

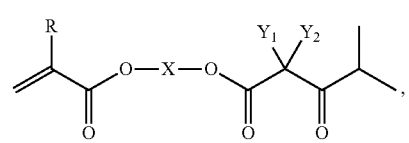

in which R is hydrogen, or a methyl group; X is a straight-chain, branched, or cyclic alkyl or alkyl ether group having from 1 to 15 carbon atoms or aromatic group having from 6 to 15 carbon atoms; and Y1 and Y2 are independently hydrogen or an alkyl having 1 to 2 carbon atoms. Also disclosed are emulsion polymers, suspension polymers, and solution polymers that comprise residues from the substituted 3-oxopentanoate monomers, and that may also include one or more additional ethylenically unsaturated monomers. Also disclosed are coating compositions that include a latex emulsion polymer and the substituted 3-oxopentanoate monomer of formula 1 provided as a coalescent.

14 Claims, No Drawings

(56) References Cited

U.S. PATENT DOCUMENTS

| | | |
|---|---|---|
| 5,985,018 A | 11/1999 | Link et al. |
| 5,990,224 A | 11/1999 | Raynolds et al. |
| 5,998,543 A | 12/1999 | Collins et al. |
| 6,005,035 A | 12/1999 | Raynolds et al. |
| 6,025,410 A | 2/2000 | Moy et al. |
| 6,060,556 A | 5/2000 | Collins et al. |
| 6,090,882 A | 7/2000 | Trumbo |
| 6,201,048 B1 | 3/2001 | Raynolds et al. |
| 6,262,169 B1 | 7/2001 | Helmer et al. |
| 6,265,028 B1 | 7/2001 | Zhao et al. |
| 6,417,267 B1 | 7/2002 | Stockl et al. |
| 6,417,269 B1 | 7/2002 | Murray et al. |
| 6,969,734 B1 | 11/2005 | Pressley et al. |
| 7,101,921 B2 | 9/2006 | Edwards et al. |
| 7,138,438 B2 | 11/2006 | Lauer et al. |
| 2003/0134973 A1 | 7/2003 | Chen et al. |
| 2008/0194722 A1 | 8/2008 | Abuelyaman et al. |
| 2010/0081769 A1 | 4/2010 | Ma |

FOREIGN PATENT DOCUMENTS

| | | |
|---|---|---|
| EP | 0 501 614 A2 | 9/1992 |
| EP | 0 875 496 A1 | 11/1998 |
| EP | 1 070 699 A1 | 1/2001 |
| EP | 1 348 416 A1 | 10/2003 |
| GB | 2 335 424 A | 9/1999 |
| JP | 4041462 A | 2/1992 |
| JP | 4106925 A | 4/1992 |
| JP | 05273799 A | 10/1993 |
| JP | 06027750 A | 2/1994 |
| JP | 06095441 A | 4/1994 |
| JP | 06130706 A | 5/1994 |
| JP | 07084379 A | 3/1995 |
| JP | 08050380 A | 2/1996 |
| JP | 08194341 A | 7/1996 |
| JP | 11335222 A | 12/1999 |
| JP | 3274214 B2 | 4/2002 |
| JP | 2003 237246 A | 8/2003 |
| JP | 3505129 B2 | 3/2004 |
| JP | 2004 125985 A | 4/2004 |
| JP | 3588014 B2 | 11/2004 |
| WO | WO 99/58608 A1 | 11/1999 |
| WO | WO 2005/105963 A1 | 11/2005 |
| WO | WO 2007/094922 A2 | 8/2007 |

OTHER PUBLICATIONS

Witzman, J. S., et al., Comparison of Methods for the Preparation of Acetoacetylated Coating Resins, Eastman Kodak Company, Oct. 1990, vol. 62, No. 789 Presented at the 16$^{th}$ Annual Water-Borne and Higher-Solids Coatings Symposium, New Orleans, LA, Feb. 1-3, 1989.

Smith, Oliver W., et al., "New vinyl monomers for emulsion polymers", Progress in Organic Coatings, 22, (1993), pp. 19-25.

Moszner, Norbert, et al., "Reaction behavior of monomeric β-ketoesters: 2. Synthesis, characterization and polymerization of methacrylate group containing enamines", Polymer Bulletin 32, (1994) pp. 419-426.

ASTM D2369, Aug. 2011.

Notification of Transmittal of the International Search Report and the Written Opinion of the International Searching Authority, or the Declaration dated Feb. 14, 2012, International application No. PCT/US2011/0162181.

Notification of Transmittal of the International Search Report and the Written Opinion of the International Searching Authority, or the Declaration dated Feb. 9, 2012, International application No. PCT/US2011/062295.

Notification of Transmittal of the International Search Report and the Written Opinion of the International Searching Authority, or the Declaration with a mailing date of Feb. 29, 2012 and International application No. PCT/US2011/063903.

Copending U.S. Appl. No. 12/968,849, filed Dec. 15, 2010, John Thornton Maddox, et al.

Copending U.S. Appl. No. 12/968,816, filed Dec. 15, 2010, John Thornton Maddox, et al.

Office Action dated Aug. 5, 2011 in copending U.S. Appl. No. 12/986,816.

Office Action dated Jun. 7, 2012 in copending U.S. Appl. No. 12/986,816.

Office Action dated Oct. 3, 2012 in copending U.S. Appl. No. 12/986,816.

\* cited by examiner

SUBSTITUTED 3-OXOPENTANOATES AND THEIR USES IN COATING COMPOSITIONS

FIELD OF THE INVENTION

This invention relates to ethylenically unsaturated, hydrolytically-stable molecules, and in particular, to hydrolytically stable, substituted 3-oxopentanoates and their uses in coating compositions.

BACKGROUND OF THE INVENTION

Waterborne acrylic coatings can deliver performance comparable to traditional solvent-borne coatings while meeting increasingly stringent coating VOC emission regulations. It is known in the coatings art that the formation of a latex film can be facilitated by incorporating a coalescing agent in the latex emulsion. These coalescing agents, or coalescents, facilitate the individual latex particles coming together to thereby form a continuous film at a given temperature by reducing the minimum film-forming temperature (MFFT) of the latex polymer. Thus, as used throughout, the coalescents of the invention reduce the minimum film-forming temperatures of the coating compositions in which they are used, as further described below.

Acetoacetoxyethyl methacrylate (AAEM) is a functional monomer used to make self-crosslinking, room-temperature-cure emulsion copolymers that may be used to produce coatings having good hardness and chemical and block resistance. Once incorporated into the copolymer, the acetoacetoxy-functionality of the AAEM monomer can cross-link via an "oxidative cure" or react with an added cross-linker such as a diamine to produce a cured film.

One of the recognized drawbacks of the acetoacetoxy moiety of AAEM is that it is known to be hydrolytically labile and a decline in film performance of copolymers prepared from this monomer has been correlated with the heat history and age of the copolymers. To avoid this degradation in performance, manufacturers have added volatile amines to convert the acetoacetate to its enamine tautomer and limit the hydrolysis. While this slows the hydrolysis, it does not completely eliminate it. Also, the addition of a volatile amine component can introduce a disagreeable odor to the coating product during application.

U.S. Pat. No. 4,215,195 to Ponticello et al. discloses compounds, including methacrylamides and acetoacetamidoethyl methacrylate, that can be homopolymerized or copolymerized with each other or with polymerizable ethylenically unsaturated monomers to give crosslinkable polymers. Polymers made from monomers having amide functionality are said to exhibit improved hydrolytic stability.

U.S. Pat. Nos. 4,855,349 and 5,073,445 to Ingle disclose permanently flexible and non-tacky coating mastic and caulking compositions that contain one or more polymers having a $T_g$ of about $-50°$ C. to about $-10°$ C. and pendant functional groups attached to the polymer backbone having the formula $-R_1-C=O-CH_2-X$, in which $R_1$ is a divalent organic radical at least 3 atoms in length, and X is organoacyl or cyano. Acetoacetoxy-ethyl methacrylate is exemplified.

U.S. Pat. No. 5,296,530 to Bors et al. discloses a method for light-assisted curing of coatings by providing coatings with an enamine content sufficient to enhance the cure rate of the coatings. According to the disclosure, a quick-curing coating is prepared from a polymer having acetoacetyl groups, in which substantially all of the acetoacetyl groups have been converted to enamine functionality, for example by treatment with ammonia or primary amine. Coatings which are so prepared are said to cure more quickly under sunlight or ultraviolet light than coatings which contain the acetoacetyl functional polymer which has not been converted to enamine. Acetoacetoxy-ethyl methacrylate is exemplified.

U.S. Pat. No. 5,494,975 to Lavoie et al. discloses the preparation of polymers containing functional acetoacetate groups and then, following the polymerization, reacting the acetoacetate group with a functional amine to form an enamine. A preferred monomer is acetoacetoxyethyl methacrylate. Examples of other monomers said to be useful for introduction of acetoacetate functionality include acetoacetoxyethyl acrylate, acetoacetoxypropyl methacrylate, allyl acetoacetate, acetoacetoxybutyl methacrylate, and 2,3-di(acetoacetoxy)propyl methacrylate.

U.S. Pat. No. 5,484,849 to Bors et al. discloses air curing polymer compositions which contain an acetoacetate-functional polymer and an autoxidizable material. The compositions cure on exposure to oxygen. The acetoacetate-functional polymers can be prepared by means known in the art. A preferred method is polymerization through incorporation which includes an acetoacetate-functional monomer, with acetoacetoxy-ethyl methacrylate, acetoacetoxypropyl methacrylate, and allyl acetoacetate being exemplified. Examples of other monomers said to be useful include acetoacetoxy-ethyl acrylate, acetoacetoxybutyl methacrylate, and 2,3-di (acetoacetoxy)propyl methacrylate.

J. Stewart Witzeman et al. reported that acetoacetylated polymers and resins have been shown to be capable of undergoing a variety of crosslinking reactions, and that the best industrial method for acetoacetylation of monomeric and polymeric materials is by transesterification with t-butyl acetoacetate. They also reported that among the processes which have been used to effect crosslinking of acetoacetylated polymeric materials are reactions with diamines, melamine, aldehydes, isocyanates, chelation with metals, and Michael reaction with activated olefins. They further reported that acetoacetylated materials can be prepared by treating a nucleophile with diketene, from the thermal reaction of 2,2,6-trimethyl-4H-1,3,-dioxin-4-one, TKD, the diketene-acetone adduct, or by transesterification with another acetoacetate. See *Comparison of Methods for the Preparation of Acetoacetylated Coating Resins*, Witzeman, J. S.; Dell Nottingham, W.; Del Rector, F. J. Coatings Technology; Vol. 62, 1990, 10 1.

U.S. Pat. No. 5,756,826 to Hanselmann discloses a process for preparing acetoacetates, in which (2-acetoacetamido-2-methylpropyl)methacrylate may be formed by reacting 2-amino-2-methyl-1-propanol with diketene, the adduct then being reacted with thiodiphenylamine and methacrylic anhydride, followed by further thiodiphenylamine to form the (2-acetoacetamido-2-methylpropyl)methacrylate. Alternatively, the reaction may be carried out in a similar method, but using different alcohols.

U.S. Pat. No. 5,872,297 to Trumbo discloses ethylenically-unsaturated 1,3-diketoamide functional compounds, polymers comprised thereof, and latex formulations containing polymeric ingredients having 1,3-diketoamide functional pendant moieties. The 1,3-diketoamide functional pendant moieties are said to have excellent hydrolytic stability.

U.S. Pat. Nos. 5,945,489 and 6,025,410 to Moy et al. disclose liquid oligomeric compositions made by the Michael addition reaction of acetoacetate functional donor compounds with multifunctional acrylate receptor compounds where the equivalent ratios of multifunctional acrylate to acetoacetate vary from greater than or equal to 1:1 to greater than or equal to 13.2:1, depending on the functionality of both multifunctional acrylate and acetoacetate. The use of multifunctional (diacrylates, triacrylates, and tetraacrylates) acrylates results in residual unsaturation in the oligomers that is useful for subsequent cross-linking. The liquid oligomers may thus be further crosslinked to make coatings, laminates and adhesives.

U.S. Pat. No. 5,990,224 to Raynolds et al. discloses low foam waterborne polymer compositions stabilized against gelling due to the addition of a poly(alkylenimine) by addition of surfactants. Enamine-functional polymers are said to represent a preferred embodiment of polymers, and may be prepared by reacting a polymer having acetoacetoxy groups with ammonia or a primary or secondary amine, such as polyethylenimine (PEI). Acetoacetoxy-type functional polymers are said to be useful, and may be prepared by free radical emulsion polymerization of vinyl monomers having an acetoacetoxy functionality with other vinyl monomers. Preferred monomers of this type are said to include acetoacetoxy-ethyl methacrylate, acetoacetoxyethyl acrylate, acetoacetoxy(methyl)ethyl acrylate, acetoacetoxypropyl acrylate, allyl acetoacetate, acetoacetamido-ethyl(meth)acrylate, and acetoacetoxybutyl acrylate, with acetoacetoxyethyl methacrylate (AAEM) representing a particularly preferred such monomer. Acetoacetoxyethyl methacrylate is the monomer used in the examples.

U.S. Pat. No. 5,962,556 to Taylor discloses the use of a monomer represented by formula:

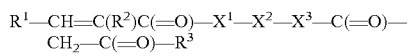

where $R^1$ is a hydrogen or halogen; $R^2$ is a hydrogen, halogen, $C_1$-$C_6$ alkylthio group, or $C_1$-$C_6$ alkyl group; $R^3$ is a $C_1$-$C_6$ alkyl group; $X^1$ and $X^3$ are independently O, S or a group of the formula: —N($R^1$)—, where $R^1$ is a $C_1$-$C_6$ alkyl group; $X^2$ is a $C_2$-$C_{12}$ alkylene group or $C_3$-$C_{12}$ cycloalkylene group. The alkyl and alkylene group described may be straight or branched. Preferred monomers are said to include acetoacetoxyethyl (meth)acrylate, acetoacetoxy(methyl)ethyl (meth)acrylate, acetoacetoxypropyl(meth)acrylate and acetoacetoxybutyl (meth)acrylate, with the term "(meth)acrylate" used in the patent to denote methacrylate or acrylate. The only such monomer exemplified is acetoacetoxyethyl methacrylate. U.S. Pat. No. 6,262,169 to Helmer et al., and U.S. Pat. Publn. No. 2003/0134973A1 to Chen et al., likewise disclose polymers having acetoacetoxy functional groups.

GB 2 335 424A, related to curable compounds and polymers having reactive functional groups, discloses an unsaturated compound (A), that can be 2-aceto-acetoxyethyl methacrylate, 3-acetoacetoxypropyl methacrylate, allyl acetoacetate, or an acetoacetate of a polyol such as trimethylol propane or pentaerythritol, reacted with a compound (B) which can be inter alia an acrylate for example having epoxide functionality, an acrylamide, or a maleate diester, to obtain a compound that can, itself, be used as a monomer, or further reacted with another compound having an activated double bond. For example, according to the disclosure, acetoacetoxyethyl methacrylate is reacted with glycidyl acrylate to produce bis(carboglycidoxyethyl)acetoacetoxyethyl methacrylate, and dimethyl malonate is reacted with neopentyl glycol to produce a neopentyl malonate polyester. A further disclosure is trimethylolpropane reacted with t-butyl acetoacetate to form 1,1,1-tris(acetoacetoxymethyl)propane.

U.S. Pat. Publn. No. 2008/0194722 discloses a hardenable dental composition that includes a polymerizable compound having at least one cyclic allylic sulfide moiety and at least one (meth)acryloyl moiety. The polymerizable compound is referred to as a hybrid monomer or a hybrid compound, and can be a substituted acetoacetoxyethyl methacrylate. See Formula 1a-5. The hardenable component is one that is capable of polymerization and/or crosslinking reactions including, for example, photopolymerization reactions and chemical polymerization techniques (e.g., ionic reactions or chemical reactions forming radicals effective to polymerize ethylenically unsaturated compounds, (meth)acrylate compounds, etc.) involving one or more compounds capable of hardening. Hardening reactions are also said to include acid-base setting reactions such as those common for cement forming compositions (e.g., zinc polycarboxylate cements, glass-ionomer cements, etc.).

U.S. Pat. Publn. No. 2010/0081769 discloses a process for producing a linear block copolymer, useful as a dispersant for pigment, wherein the block copolymer comprises acetoacetyl amine functional groups which serve as pigment anchoring groups. The acetoacetyl amine functional groups can be formed by reacting hydroxyl functional groups with an acetoacetate agent, and then reacting the resulting acetoacetate functional groups with a primary amine. One example of ethylenically unsaturated acetoacetate monomers that is useful for introduction of acetoacetate functional group into the block copolymer can be acetoacetoxyethyl methacrylate. Examples of other monomers that can be used to introduce an acetoacetate functional group into the block copolymer can include acetoacetoxyethyl acrylate, acetoacetoxypropyl methacrylate, acetoacetoxypropyl acrylate, allyl acetoacetate, acetoacetoxybutyl methacrylate, acetoacetoxybutyl acrylate, and the like.

Though acetoacetoxy-functional monomers are known to be useful in polymerization processes, and the polymers and copolymers made from such processes find use in coating compositions, there remains a need in the art for monomers useful in coating compositions, whether UV-curable monomer mixtures, solution acrylics, or emulsion polymers known as latexes, and that may be used to produce coatings having good hardness and chemical and block resistance, and that exhibit improved hydrolytic stability. It would be an additional advantage if such molecules might be used as coalescents, provided as mixtures with latex emulsion polymers to provide coating compositions having improved coalescing properties.

SUMMARY OF THE INVENTION

In one aspect, the invention relates to substituted 3-oxopentanoates corresponding to the following formula 1:

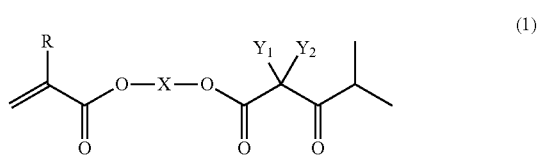

in which R is hydrogen or a methyl group; X is a straight-chain, branched, or cyclic alkyl or alkyl ether group having from 1 to 15 carbon atoms or aromatic group having from 6 to 15 carbon atoms; and Y1 and Y2 are independently hydrogen or an alkyl having 1 to 2 carbon atoms. In one aspect, X may comprise a branched or straight chain alkyl or alkyl ether group having from 1 to 8 carbon atoms. In another aspect, X may comprise a cyclic alkyl or alkyl ether having from 6 to 8 carbon atoms. In yet another aspect, X may comprise an aromatic group having from 6 to 15 carbon atoms.

In yet another aspect, the invention relates to a substituted 3-oxopentanoate corresponding to formula 1, wherein X has one of the following structures:

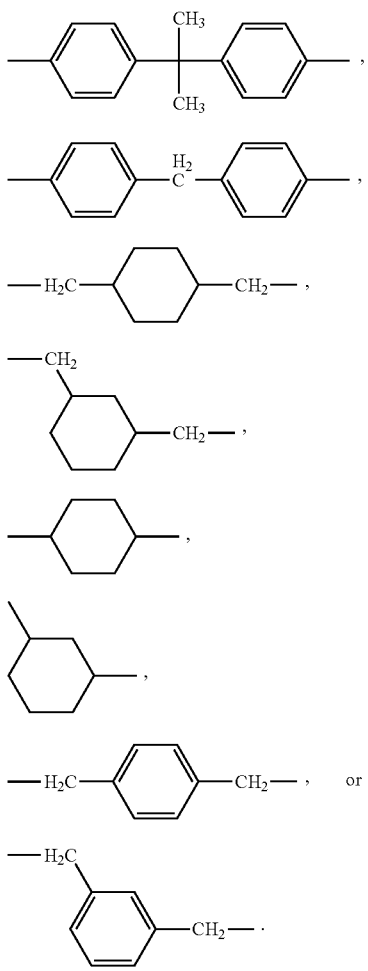

In a further aspect, the invention relates to a substituted 3-oxopentanoate corresponding to formula 1, wherein R is hydrogen or methyl; X is alkyl or alkyl ether having 2 to 6 carbon atoms; and Y1 and Y2 are methyl. Alternatively, R may be methyl; X ethyl; and Y1 and Y2 methyl. In yet another aspect, R may be methyl; X dimethylpropyl; and Y1 and Y2 methyl.

In yet another aspect, the invention relates to an ethylenically unsaturated substituted 3-oxopentanoate corresponding to the following structure:

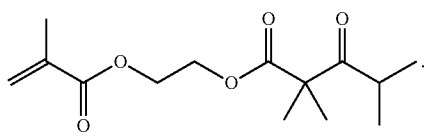

In a further aspect, the invention relates to an ethylenically unsaturated substituted 3-oxopentanoate corresponding to the following structure:

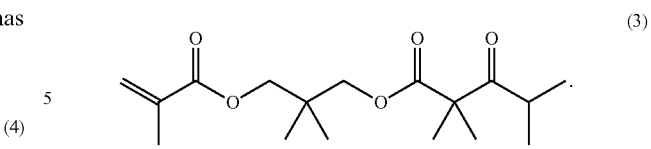

In yet another aspect, the invention relates to an emulsion polymer comprising residues from a substituted 3-oxopentanoate of formula 1 and residues from one or more additional ethylenically unsaturated monomers. In a further aspect, the one or more additional ethylenically unsaturated monomers comprise one or more of: methyl (meth)acrylate, ethyl (meth)acrylate, propyl(meth)acrylate, isopropyl (meth)acrylate, butyl (meth)acrylate, isobutyl (meth)acrylate, hexyl(meth)acrylate, isooctyl(meth)acrylate, isodecyl(meth)acrylate, lauryl(meth)acrylate, stearyl (meth)acrylate, phenoxyethyl (meth)acrylate, methoxyethyl (meth)acrylate, benzyl (meth)acrylate, ethoxyethyl (meth)acrylate, 2-ethylhexyl (meth)acrylate, cyclopentyl (meth)acrylate, isobutyl (meth)acrylate, styrene, p-methyl styrene, o-methyl styrene, p-butyl styrene, or alpha-methyl styrene.

In yet another aspect, the invention relates to a solution polymer comprising residues from the substituted 3-oxopentanoate of formula 1. In a further aspect, the invention relates to a coating composition comprising the substituted 3-oxopentanoate of formula 1, optionally with one or more additional ethylenically unsaturated monomers. In a further aspect, the invention relates to a coating composition comprising a latex emulsion polymer, with the substituted 3-oxopentanoate of formula 1 provided in an admixture as a coalescent, or as a reactive coalescent. In yet another aspect, the invention relates to a latex formulation comprising a polymer having residues from the substituted 3-oxopentanoate of formula 1 dispersed in an evaporable aqueous carrier. Other aspects of the invention are as disclosed and claimed herein.

DETAILED DESCRIPTION OF THE INVENTION

In one aspect, the invention relates to ethylenically unsaturated, substituted 3-oxopentanoates, useful in coating compositions. The ethylenically unsaturated, substituted 3-oxopentanoates according to the invention are also described herein as "monomers," although those skilled in the art will understand from the disclosure that these molecules find use, not just as residues incorporated into polymers, but also provided in unreacted form, either as self-initiating monomers or as coalescents used in admixtures with latex emulsion polymers.

Not wishing to be bound by any theory, the development of harder films observed upon curing and described herein appears to result from a chemical reaction, so that the coalescents described herein may be described as reactive coalescents. Coalescing agents, or coalescents, facilitate the individual latex particles coming together to thereby form a continuous film at a given temperature by reducing the minimum film-forming temperature (MFFT) of the latex polymer. Thus, as used herein, the substituted 3-oxopentanoates of the invention act as coalescents by reducing the minimum film-forming temperatures of the coating compositions in which they are used.

In one aspect, the ethylenically unsaturated, substituted 3-oxopentanoates of the invention correspond to the following formula 1:

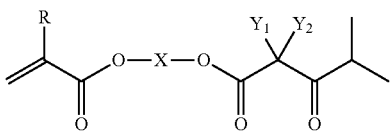

(1)

in which R is hydrogen, or a methyl group;

X is a straight-chain, branched, or cyclic alkyl, alkyl ether, or aromatic group having from 1 to 15 carbon atoms; and Y1 and Y2 are independently hydrogen or an alkyl having 1 to 2 carbon atoms.

In another aspect, the invention relates to substituted 3-oxopentanoates, useful for preparing coating compositions, that correspond to formula 1 above, wherein X is a straight-chain, branched, or cyclic alkyl, alkyl ether, or aromatic group having 1 to 15 carbon atoms.

In another aspect, the invention relates to substituted 3-oxopentanoates, useful for preparing coating compositions, that correspond to formula 1 above, wherein R is hydrogen or methyl; X is alkyl or alkyl ether having 2 to 6 carbon atoms; and Y1 and Y2 are methyl.

In yet another aspect, the invention relates to substituted 3-oxopentanoates, useful for preparing coating compositions, that correspond to formula 1 above, wherein R is methyl; X is ethyl or ethoxy-ethyl (that is, a diethylene glycol residue); and Y1 and Y2 are methyl.

In yet another aspect, the invention relates to substituted 3-oxopentanoates, useful for preparing coating compositions, that correspond to formula 1 above, wherein R is methyl; X is dimethylpropyl or ethoxy-ethoxy-ethyl (that is, a triethylene glycol residue); and Y1 and Y2 are methyl.

In yet another aspect, the invention relates to the ethylenically unsaturated, substituted 3-oxopentanoates just described, that is, simply to the molecules themselves, and specifically to 2-(methacryloyloxy)ethyl 2,2,4-trimethyl-3-oxopentanoate and to 3-(methacryloyloxy)-2,2-dimethylpropyl 2,2,4-trimethyl-3-oxopentanoate, having, respectively, the following structures:

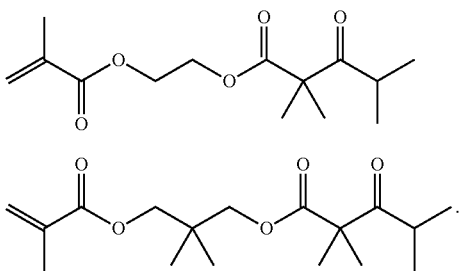

(2)

(3)

In another aspect, the invention relates to ethylenically unsaturated, substituted 3-oxopentanoatescorresponding to the following formula 1:

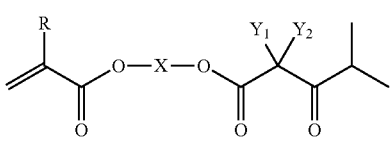

(1)

in which R is hydrogen, or a methyl group;

X has one of the following structures:

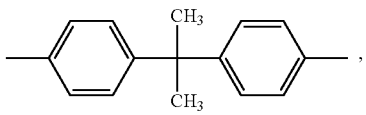

(4)

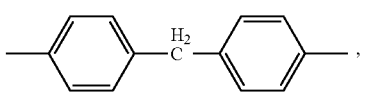

(5)

(6)

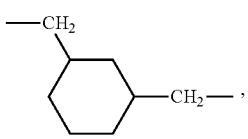

(7)

(8)

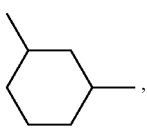

(9)

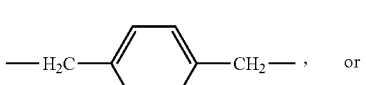

(10)

or

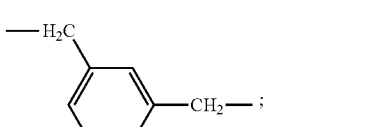

(11)

and Y1 and Y2 are independently hydrogen or an alkyl having 1 to 2 carbon atoms. Thus, according to the invention, the X group of formula 1 may be selected from a large group of diol residues, and the scope of the invention is not intended to be especially limited in terms of the diol chosen.

In yet another aspect, the invention relates to homopolymers and copolymers of the above-referenced substituted 3-oxopentanoates, for example made using emulsion polymerization or solution acrylic processes, that are useful as or in coating compositions, for example to make self-initiating UV curable polymers possessing hydrolytic stability.

In yet another aspect, the invention relates to one or more of the above-referenced substituted 3-oxopentanoates, alone or with other known ethylenically unsaturated, or vinyl, monomers, that serve as coating compositions which readily polymerize via UV-cure, as further described herein. These mixtures may include an organic solvent, or may simply be mixtures of the monomers themselves, that cure upon exposure to UV light, with or without the use of photoinitiators.

Thus, the invention is also directed to polymers derived from at least one of the substituted 3-oxopentanoate monomers set out herein. The polymer may be a homopolymer, or a copolymer of the monomer and one or more additional copolymerizable monomers. The polymer may be a solution polymer, or may alternatively be a suspension polymer or a latex formed via emulsion polymerization, as set forth herein.

The polymers according to the invention are derived from the substituted 3-oxopentanoate monomers of the invention, and are addition polymers that may be formed via a free-radical addition polymerization. In such addition polymers, the propagating species may be a free radical, and the polymer is formed in a chain-growth fashion polymerization as understood in the art. As noted, these polymers may be solution polymers, in which the monomers are polymerized in an inert solvent via a free-radical polymerization. Alternatively, the polymers may be latex polymers in which a monomer solution is emulsified in an aqueous solution, and under agitation is reacted via a free-radical polymerization process as described herein, to form latex particles. In a further alternative, the polymers may be suspension polymers, in which the monomers are suspended in a continuous aqueous phase, the suspension polymers being most easily distinguished from the latex particles by particle size and intended use. In yet another alternative, the substituted 3-oxopentanoates of the invention may be directly applied as a coating composition, alone or with other ethylenically-unsaturated monomers, with or without a free radical initiator, and free-radical polymerized to form a coating. In yet a further alternative, the substituted 3-oxopentanoates of the invention may be used as coalescents, in admixture for example with latex emulsion polymers, and appear to function as reactive coalescents, although we do not wish to be bound by this observation.

The present invention is thus also directed to latex formulations containing a polymer having substituted 3-oxopentanoate functional pendant moieties derived from the substituted 3-oxopentanoates of the invention, dispersed in an evaporable aqueous carrier. The substituted 3-oxopentanoates employed in the polymers and latex formulations of this invention advantageously exhibit excellent hydrolytic stability so that such formulations can be stored for long periods of time without degradation of the substituted 3-oxopentanoate functionality. Additionally, the substituted 3-oxopentanoates employed in the polymers and latex formulations of this invention advantageously exhibit the ability to crosslink using ultraviolet light, even without the addition of costly photoinitiators, although such photoinitiators may optionally be used.

Ethylenically Unsaturated Substituted 3-Oxopentanoates

The ethylenically unsaturated substituted 3-oxopentanoates of the present invention are characterized as being useful as ethylenically unsaturated monomers that can participate in addition polymerization reactions, alone or with other known ethylenically unsaturated monomers. As used herein, ethylenically unsaturated monomers are also described as vinyl monomers, and with respect to the solution polymers, the suspension polymers, and the latex or emulsion polymers described herein, vinyl monomers and ethylenically unsaturated monomers shall be considered interchangeable terms. The polymers made from such monomers are thus addition polymers, and may be formed as solution acrylic polymers, or as suspension polymers or as emulsion polymers, also known as latexes. Alternatively the monomers of the present invention may be provided alone, or as monomer mixtures, and may serve as coating compositions which, once applied, self-cure to form a coating, as further set out in the present description and the examples. The ethylenically unsaturated substituted 3-oxopentanoates of the present invention are further characterized as being useful as coalescents in coating compositions that include a latex emulsion polymer.

The ethylenically unsaturated substituted 3-oxopentanoates of the invention may be prepared, for example, by reacting a suitable glycol or glycol ether with 2,2,4,4-tetramethyl-1,3-cyclobutanedione to install the 3-oxpentanoate moiety, followed by reaction with a reagent such as methacrylic anhydride to install the ethylenically unsaturated moiety. Alternatively, the ethylenically unsaturated substituted 3-oxopentanoates of the invention may be prepared by first reacting a suitable glycol or glycol ether with a reagent such as methacrylic anhydride to install the ethylenically unsaturated moiety, followed by reaction with 2,2,4,4-tetramethyl-1,3-cyclobutanedione to install the 3-oxpentanoate moiety.

When we say that the polymers according to the invention have pendant moieties, we mean that the ethylenically unsaturated monomers of the invention have been reacted into an addition polymer, and that a portion of the monomers remains as a pendant moiety. Alternatively, we may say that the polymers according to the invention have residues from the ethylenically unsaturated monomers of the invention, in which case we mean that the monomers have been reacted into an addition polymer via their ethylenic unsaturation, and that a portion of the monomers remains as a residue. Both these descriptions are well-known in the art of addition polymers, and the descriptions are not otherwise intended to be especially limiting.

When we say that the ethylenically unsaturated substituted 3-oxopentanoates of the invention are useful in coating compositions, we do not intend this phrase to be especially limiting. For example, we mean that they may be used alone or with other ethylenically unsaturated monomers to form monomer solutions that readily polymerize under desired conditions. Alternatively, the ethylenically unsaturated substituted 3-oxopentanoates of the invention may be used alone or together with other ethylenically unsaturated monomers to form addition polymers, whether as solution acrylics or emulsion polymers known as latexes. The ethylenically unsaturated substituted 3-oxopentanoates of the present invention are also useful as coalescents in coating compositions that include a latex emulsion polymer.

Emulsion Polymers Made from the Ethylenically Unsaturated Substituted 3-Oxopentanoate Monomers In one aspect, the invention thus relates to emulsion polymers containing residues from the inventive ethylenically unsaturated substituted 3-oxopentanoates of the invention, which are also known as latexes. In these latexes, the polymers formed may have a particle size ranging, for example, from about 80 to about 300 nm, or from 100 nm to 250 nm, or from 125 nm to 200 nm. The $T_g$ of such latexes may range, for example, from about 0° C. to about 80° C., or from 15° C. to 60° C., or from 20° C. to 40° C.

The latex polymer compositions in accordance with the present invention may be prepared by an emulsion or suspension free radical polymerization of ethylenically unsaturated monomers that include the substituted 3-oxopentanoates of the invention. These latex polymers may be homopolymers, or may be copolymers of the substituted 3-oxopentanoates of the invention and other ethylenically unsaturated monomers.

Examples of other ethylenically unsaturated comonomers include, but are not limited to, acrylic and methacrylic acid esters such as methyl (meth)acrylate, ethyl (meth)acrylate, propyl(meth)acrylate, isopropyl(meth)acrylate, butyl (meth)acrylate, isobutyl (meth)acrylate, hexyl(meth)acrylate, isooctyl(meth)acrylate, isodecyl (meth)acrylate, lauryl (meth)acrylate, stearyl(meth)acrylate, phenoxyethyl (meth)acrylate, methoxyethyl (meth)acrylate, benzyl (meth)acrylate, ethoxyethyl (meth)acrylate, 2-ethylhexyl (meth)acrylate, cyclopentyl(meth)acrylate and isobutyl (meth)

acrylate, as well as combinations of these monomers. A combination of these monomers may be used in order to achieve an appropriate Tg or other properties for the functional latex polymer.

Such acrylic and methacrylic acid esters having a C1-C20 alcohol moiety are commercially available or can be prepared by known esterification processes. The acrylic and methacrylic acid ester may contain additional functional groups, such as, hydroxyl, amine, halogen, ether, carboxylic acid, amide, nitrile, and alkyl group. Such esters include carbodiimide(meth)acrylate, methyl (meth)acrylate, ethyl (meth)acrylate, butyl (meth)acrylate, isobutyl (meth)acrylate, ethylhexyl (meth)acrylate, octyl(meth)acrylate, isobutyl (meth)acrylate, allyl(meth)acrylate, and glycidyl(meth)acrylate.

Additional suitable copolymerizable ethylenically unsaturated monomers include styrenic monomers. Styrenic monomers include styrene, as well as substituted styrenes such as C1-C6 alkyl ring-substituted styrene, C1-C3 alkyl alpha-substituted styrene or a combination of ring and an alpha-alkyl substituted styrene. Such styrenic copolymerizable monomers include styrene, p-methyl styrene, o-methyl styrene, p-butyl styrene, alpha-methyl styrene, and combinations thereof.

In addition, vinyl esters may be used as copolymerizable monoethylenically unsaturated monomers, including vinyl esters of vinyl alcohol such as the VEOVA series available from Shell Chemical Company as VEOVA 5, VEOVA 9, VEOVA 10, and VEOVA 11 products. See O. W. Smith, M. J. Collins, P. S. Martin, and D. R. Bassett, Prog. Org. Coatings 22, 19 (1993).

In general, the vinyl monomers may be polymerized by a conventional suspension or emulsion free-radical initiated polymerization technique. The polymerization can be initiated by a water-soluble or water-dispersible free-radical initiator, optionally in combination with a reducing agent, at an appropriate temperature, for example from 55 to 90° C. The polymerization of the monomers may be conducted batch wise, semi-batch or in a continuous mode.

A conventional surfactant or a combination of surfactants may be used such as anionic or non-ionic emulsifier in the suspension or emulsion polymerization to prepare a polymer of the invention. Examples of such surfactants include, but are not limited to, alkali or ammonium alkylsulfate, alkylsulfonic acid, or fatty acid, oxyethylated alkylphenol, or any combination of anionic or non-ionic surfactant. A surfactant monomer may be used such as HITENOL HS-20 (which is a polyoxyethylene alkylphenyl ether ammonium sulfate available from DKS International, Inc., Japan). A list of surfactants is available in the treatise: McCutcheon's Emulsifiers & Detergents, North American Edition and International Edition, MC Publishing Co., Glen Rock, N.J. 1993. The amount of the surfactant used is usually between 0.1 to 6 wt %, based on the total weight of the monomers.

As polymerization initiators, any conventional free-radical initiator may be used such as hydrogen peroxide, t-butylhydroperoxide, ammonium or alkali sulfate, di-benzoyl peroxide, lauryl peroxide, di-tertiarybutylperoxide, 2,2'-azobisisobutyronitrile, benzoyl peroxide, and the like. The amount of the initiator is typically between 0.05 to 6.0 wt %, based on the total weight of the total monomers.

A free-radical initiator may be combined with a reducing agent to form a redox initiating system. Suitable reducing agents are those which increase the rate of polymerization and include, for example, sodium bisulfite, sodium hydrosulfide, sodium ascorbic acid, isoascorbic acid and mixtures thereof. The redox initiating system can be used at similar levels as the free-radical initiators.

In addition, in combination with the initiators and reducing agents, polymerization catalysts may be used. Polymerization catalysts are those compounds which increase the rate of polymerization by promoting decomposition of the free radical initiator in combination with the reducing agent at the reaction conditions. Suitable catalysts include transition metal compounds such as, for example, ferrous sulfate heptahydrate, ferrous chloride, cupric sulfate, cupric chloride, cobalt acetate, cobaltous sulfate, and mixtures thereof.

In addition, a low level of a chain transfer agent may also be used to prepare a polymer in accordance with the invention. Suitable chain transfer agents include, but are not limited to, butyl mercaptan, n-octylmercaptan, n-dodecyl mercaptan, butyl or methyl mercaptopropionate, mercaptopropionic acid, 2-ethylhexyl 3-mercaptopropionate, n-butyl 3-mercaptopropionate, isodecylmercaptan, octadecylmercaptan, mercaptoacetic acid, haloalkyl compounds, (such as carbon tetrabromide and bromodichloromethane), and the reactive chain transfer agents described in U.S. Pat. No. 5,247,040, incorporated herein by reference. In particular, mercaptopropionate, allyl mercaptopropionate, allyl mercaptoacetate, crotyl mercaptopropionate and crotyl mercaptoacetate, and mixtures thereof, represent preferred chain transfer agents.

A copolymerizable monomer known to promote wet adhesion may also be incorporated into the polymer. Examples of wet adhesion promoting monomers include, but are not limited to, nitrogen-containing monomers such as t-butylaminoethyl methacrylate, dimethylaminoethyl methacrylate, diethylaminoethyl methacrylate, N,N-dimethylaminopropyl methacrylamide, 2-t-butylaminoethyl methacrylate, N,N-dimethylaminoethyl acrylate and N-(2-methacryloyloxyethyl)ethylene urea.

Water-dispersible and water-soluble polymers may also be employed as surfactants or stabilizers in accordance with the present invention. Examples of such polymeric stabilizers include water-dispersible polyesters as described in U.S. Pat. Nos. 4,946,932 and 4,939,233; water-dispersible polyurethanes as described in U.S. Pat. Nos. 4,927,876 and 5,137, 961; and alkali-soluble acrylic resins as described in U.S. Pat. No. 4,839,413, all of which are incorporated herein by reference. Cellulosics and polyvinyl alcohols may also be used. Surfactants and stabilizers may be used during the polymerization to control, for example, particle nucleation and growth, particle size and stability or they may be post added to enhance stability of the latex or modify other properties of the latex such as surface tension, wettability and the like.

In an embodiment, at least one ethylenically unsaturated copolymerizable surfactant may be employed, for example those possessing isopropenyl phenyl or allyl groups. Copolymerizable surfactants may be anionic, such as containing a sulfate or sulfonate group, or nonionic surfactants. Other copolymerizable surfactants include those containing polyoxyethylene alkyl phenyl ether moieties. Additional copolymerizable surfactants include sodium alkyl allyl sulfosuccinate. Further, the ethylenically unsaturated substituted 3-oxopentanoates of the present invention may themselves be used as coalescents, in coating compositions that include one or more latex emulsion polymers, as further described herein.

The latex polymers in accordance with the invention may have a weight average molecular weight (Mw), for example, of from 1,000 to 1,000,000, as determined by gel permeation chromatography (GPC), or from 5,000 to 250,000.

The particle size for the aqueous dispersions in accordance with the invention may be, for example, from about 0.01 to about 25 µm, or from 0.05 to 1 µm, or from 0.075 to 500 µm. Thus, in an emulsion polymerization in accordance with the invention, the particle size of the latex may range, for example, from 0.01 to 5 µm. On the other hand, in a suspension polymerization in accordance with the invention, the latex particle size may range, for example, from 2 to 25 µm, or from 3 to 20 µm, or from 4 to 15 µm.

The latex particles generally have a spherical shape, and the spherical polymeric particles may have a core portion and a shell portion or a gradient structure. The core/shell polymer particles may also be prepared in a multi-lobe form, a peanut shell, an acorn form, a raspberry form or any other form. If the particles have a core/shell structure, the core portion may comprise from about 20 to about 80 wt % of the total weight of the particle, and the shell portion may comprise about 80 to about 20 wt % of the total weight of the particle.

The glass transition temperature (Tg) of the latex polymers in accordance with the present invention, may be up to about 100° C. In a preferred embodiment of the present invention, where a film forming at ambient temperatures of the particles is desirable, the glass transition temperature may preferably be under 60° C.

The latex polymers of the invention may comprise enamine functional polymers, with the enamine functionality serving to improve the hydrolytic stability of the acetoacetoxy group. Enamine functional polymers have been described in Polymer Bulletin 32, 419-426 (1994). Additionally, enamine functional polymers are described in European Patent Application No. 0492847 A2; U.S. Pat. Nos. 5,296,530; and 5,484,849, all of which are incorporated herein by reference.

A latex polymer formed from the inventive ethylenically unsaturated substituted 3-oxopentanoates of the invention may likewise be, for example, the emulsion polymerization product of:

(i) from about 0.5 to about 30 wt % of one or more substituted 3-oxopentanoate monomers, or from 2 to 25 wt %, or from 5 to 20 wt %;

(ii) from 0 to about 6 wt % of a carboxylic acid-functional vinyl monomer, with a preferred range of about 0.5 to about 4 wt %; and (iii) from about 40 to about 99.5 wt % of additional monomers that are non-acid, and that are not substituted 3-oxopentanoate monomers, alternatively from 60 to 99 wt %.

A latex polymer of the invention containing residues from the substituted 3-oxopentanoates of the invention may also contain (iv) about 0.5 to about 5 wt % of a non-self polymerizing, surface-active vinyl monomer, preferably about 1.0 to about 3.0 wt %, and (v) about 0.1 to about 10 wt % of an adhesion-promoting monomer. The wt % is based on the total amount of monomer.

The acid-functional vinyl monomers used may be selected broadly from carboxylic acids, phosphonic acids, acid anhydrides, phosphate monomers, and other functionalities which are capable of reacting with a base to form a salt. Examples of suitable carboxylic acid-functional vinyl monomers, or vinyl monomers capable of providing carboxylic acid-functionality, include, but are not limited to, acrylic acid, methacrylic acid, itaconic acid, itaconic anhydride, citraconic acid, citraconic anhydride, and maleic anhydride. Acrylic acid, methacrylic acid, itaconic acid and maleic anhydride represent preferred carboxylic acid-functional monomers, or monomers capable of providing carboxylic acid-functionality.

Specific examples of suitable vinyl monomers that are not acids, and that are not substituted 3-oxopentanoate monomers, include, but are not limited to, methyl (meth)acrylate, ethyl (meth)acrylate, butyl (meth)acrylate, hexyl(methacrylate), isooctyl (methacrylate), isodecyl(meth)acrylate, lauryl (meth)acrylate, stearyl(meth)acrylate, phenoxyethyl (meth) acrylate, methoxyethyl (meth)acrylate, benzyl (meth) acrylate, furyl (meth)acrylate, methylfuryl(meth)acrylate, butylfuryl(meth)acrylate, tetrahydrofuryl (meth)acrylate, ethoxyethyl (meth)acrylate, 2-ethylhexyl(meth)acrylate, cyclopentyl (meth)acrylate, isobornyl(meth)acrylate, hydroxyethyl (meth)acrylate, hydroxypropyl (meth)acrylate, and combinations or mixtures thereof. Others include styrene derivatives and vinyl derivatives. Examples of suitable styrene derivatives include, but are not limited to, styrene, vinyl toluene, o-methyl styrene, p-methyl styrene and m-methyl styrene. Vinyl derivatives include, but are not limited to, vinyl esters such as vinyl acetate, vinyl propionate, vinyl 2-ethylhexanoate, vinyl neononoate, vinyl neodecanoate, and vinyl esters of versatic acid. Such monomers are described in The Brandon Worldwide Monomer Reference Guide and Sourcebook, Second Edition, 1992, Brandon Associates, Merrimack, N.H.; and in Polymers and Monomers, the 1996-1997 Catalog from Polyscience, Inc., Warrington, Pa.

The latexes formed may optionally be combined with an amine or with a poly(alkylenimine). Blending the acetoacetoxy-functional polymer with a poly(alkylenimine) has the advantage of imparting solvent resistance to the water-based coating composition, providing excellent hardness, gloss, gloss retention, solvent and chemical resistance, and weathering, without compromising anti-corrosion performance. Application of the coating composition to a substrate prompts crosslinking within the film composition through dehydration and resulting enamine formation through reaction of the acetoacetoxy moieties on the acetoacetoxy-functional polymer with the poly(alkylenimine). Such a coating composition may be formulated as a one-pack composition containing the blended latex, or as a two-pack system where the latex and the poly(alkylenimine) are blended prior to use.

A latex composition of the invention may be prepared by free radical emulsion polymerization of one or more substituted 3-oxopentanoate monomers such as those represented by Formula 1 above, optionally with carboxylic acid-functional vinyl monomers, and with non-acid, non-acetoacetoxy vinyl monomers. The polymerization reaction affords a water-based dispersion of polymer particles with the polymer having pendant substituted 3-oxopentanoate groups. A pendant substituted 3-oxopentanoate group is not limited to those at the termini of the polymer. Pendant 3-oxopentanoate groups also include groups attached to the polymer's backbone and available for further reaction.

In one aspect, the invention is thus directed to latex formulations containing a polymeric ingredient having at least substituted 3-oxopentanoate pendant moieties derived from the unsaturated substituted 3-oxopentanoate of formula 1 dispersed in an evaporable aqueous carrier. The substituted 3-oxopentanoate moiety employed in the polymers and latex formulations of this invention advantageously exhibit excellent hydrolytic stability so that such formulations can be stored for long periods of time without degradation of the substituted 3-oxopentanoate functionality. Additionally, the substituted 3-oxopentanoate moiety employed in the polymers and latex formulations of this invention advantageously exhibit the ability to crosslink using ultraviolet light without the addition of costly photoinitiators.

In a further aspect, the ethylenically unsaturated substituted 3-oxopentanoates of the present invention may be used as coalescents in coating compositions that include a latex emulsion polymer. In this aspect, the latex emulsion polymer with which the ethylenically unsaturated substituted 3-oxopentanoates is mixed need not itself include residues of the ethylenically unsaturated substituted 3-oxopentanoates of the invention, although such latex emulsion polymer may optionally itself include residues of the substituted 3-oxopentanoates of the invention.

In this aspect, such latex emulsion polymers that may be combined with the substituted 3-oxopentanoates of the present invention are well known in the art of coating compositions, and we do not intend the term to be especially limiting, although some latex emulsion polymers may be better suited as coating compositions, either inherently or in combination with the coalescents of the invention. Examples of commercial latex emulsion polymers useful according to this aspect of the invention include Rhoplex SG-30, Rhoplex HG-74P, Rhoplex SG-10M, Rhoplex AC2508, Ucar 626, and Ucar 379G (all available from The Dow Chemical Company), Acronal 296D (BASF Corp.), Aquamac 705 and Aquamac 588 (Hexion Specialty Chemicals), and the like.

The efficiency of a coalescent can be determined by determining the amount of the coalescent required to reduce the MFFT of a latex polymer to 40° F. (4.4° C.), which is the lowest desirable application temperature of a paint. It is generally considered unacceptable if the amount of the coalescent present in a paint formulation exceeds 20% by weight based on the solids of the latex polymer. As seen in the examples, the substituted 3-oxopentanoates of the present invention act as coalescents, reducing the MFFT of latexes with which they are mixed.

For this use, a waterborne coating composition is provided that comprises from about 1 to about 20 percent by weight, based on the solids of the latex polymer in the composition, of a substituted 3-oxopentanoate of the invention provided as a coalescent, as already described. In some instances, a preferred ratio of from 1 to 15 percent may be desired, or alternatively, from 1 to 10 percent.

Preferred examples of the substituted 3-oxopentanoates of the present invention are 2-(methacryloyloxy)ethyl 2,2,4-trimethyl-3-oxopentanoate and 3-(methacryloyloxy)-2,2-dimethylpropyl 2,2,4-trimethyl-3-oxopentanoate according to the following:

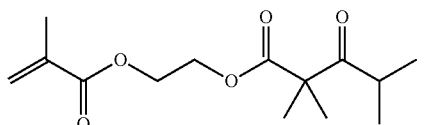

(2)

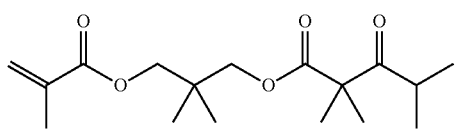

(3)

Solution Polymers Made from the Ethylenically Unsaturated Substituted 3-Oxopentanoate Monomers In another aspect, the substituted 3-oxopentanoates may be used to form homopolymers, or copolymers with the other ethylenically unsaturated monomers already described, as solution polymers. Solution polymers are addition polymers, as are the latexes or emulsion polymers just described, but are polymerized by dissolving the monomer(s) typically in a non-reactive solvent that contains a catalyst. The heat produced by the polymerization reaction is absorbed by the solvent, thus controlling the reaction rate. These solution polymers may be formed from the same ethylenically unsaturated monomers already described above with respect to suspension and emulsion polymers, and their preparation is well known to those skilled in the art of polymerization.

Simple Mixtures of Ethylenically Unsaturated Substituted 3-Oxopentanoate Monomers, and Optionally Other Ethylenically Unsaturated Monomers, as Coating Compositions We have found that the ethylenically unsaturated substituted 3-oxopentanoates of the invention may be used, alone or with other ethylenically unsaturated monomers, as coating compositions that, when applied to a substrate, form polymers to provide a coating layer on the substrate. These mixtures may be used without a photoinitiator, since the reaction appears to be a self-polymerization. For this use, also, the hydrolytic stability of the inventive monomers is a desirable feature, since the monomers will exhibit improved hydrolytic stability during storage, rather than breaking down to the decomposition products as described below with respect to AAEM.

As noted, we have also found that the ethylenically unsaturated substituted 3-oxopentanoates of the invention may be used as coalescents in coating compositions that include latex emulsion polymers, and appear to function as reactive coalescents. For this use, also, the hydrolytic stability of the substituted 3-oxopentanoates is a desirable feature, since they will exhibit improved hydrolytic stability during storage, rather than breaking down to the decomposition products as described below with respect to AAEM.

EXAMPLES

The following examples are given to illustrate the invention. It should be understood, however, that the invention is not to be limited to the specific conditions or details described in these examples.

In the examples, the following molecules were prepared, and were used alone as self-curing coating compositions; in the preparation of solution acrylic polymers; in the preparation of latex emulsions; and used as coalescents in mixtures with latex emulsions.

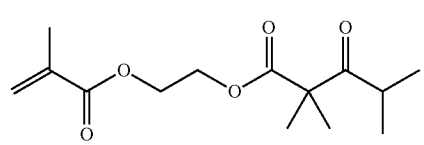

(2)

2-(methacryloyloxy)ethyl
2,2,4-trimethyl-3-oxopentanoate

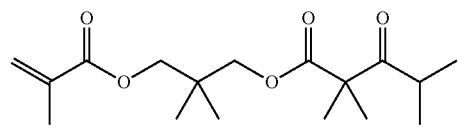

(3)

3-(methacryloyloxy)-2,2-dimethylpropyl
2,2,4-trimethyl-3-oxopentanoate

Example 1

Preparation of 2-(methacryloyloxy)ethyl
2,2,4-trimethyl-3-oxopentanoate

To a 2-L flask was charged ethylene glycol (900 mL) and 2,2,4,4-tetramethyl-1,3-cyclobutanedione (210.3 g, 1.5 moles). While using good mixing, potassium carbonate (103.5 grams, 0.75 moles) was added. An exothermic reaction resulted and the batch temperature rose to approximately 60° C. The reaction was held for 1 hour between 50-60° C. The batch was then drowned into 1500 mL demineralized water and extracted with 500 mL ethyl acetate. The ethyl acetate was evaporated at 75° C. under 6 mm Hg vacuum. The resulting crude product was distilled through a 0.5×6 inch Penn-State packed column and the vapor boiling point recorded as 94° C. (<1 mmHg). The total recovery of 2-hydroxyethyl 2,2,4-trimethyl-3-oxopentanoate was 71% with an assay of 99.5% (GC). To a 2-L flask was charged N,N-dimethylacetamide (636 g), 2-hydroxyethyl-2,2,4-trimethyl-3-oxopentanoate (318 g, 1.57 moles), DMAP (0.31 g) and triethylamine (183.2 g). The reaction was cooled to 0-5° C. and methacryloyl chloride (194.4 g, 1.88 moles) was added dropwise at <10° C. over three hours. Once addition was complete, the reaction was stirred for an additional hour at <10° C. and then warmed to 40° C. for one hour. The reaction slurry was drowned into 763 mL of demineralized water and extracted at 40° C. with 763 mL of ethyl acetate. Acetic acid (25 g) was used to aid separation of layers. The lower aqueous layer was decanted and discarded and the organic layer washed with demineralized water (763 mL). The organic layer was dried with sodium sulfate and removed with a rotary evaporator at 60° C./5 mmHg. The crude product (GC assay 82.5%) was distilled in a Kugelrohr apparatus twice at 124° C./0.05 mmHg to provide the desired product (220 g, 93% GC assay).

Example 2

Preparation of 3-(methacryloyloxy)-2,2-dimethylpropyl 2,2,4-trimethyl-3-oxopentanoate To a 1-L flask was charged 2,2,4,4-tetramethyl-1,3-cyclobutanedione (140.2 g, 1.0 moles), neopentyl glycol (208.3 g, 2 moles), potassium carbonate (138 g, 1.0 moles) and methylene chloride (500 g). The batch was refluxed for three hours then clarified to remove salts. The methylene chloride was removed with a rotary evaporator. Toluene (250 g) was added to the residue and the organic layer washed six times with 150 mL demineralized water. The organic layer was dried with sodium sulfate and the solvent removed with a rotary evaporator at 75° C./3 mmHg to provide 3-hydroxy-2,2-dimethylpropyl 2,2,4-trimethyl-3-oxopentanoate (244 g, 96.3% GC assay). To a 2-L flask was charged 3-hydroxy-2,2-dimethylpropyl 2,2,4-trimethyl-3-oxopentanoate (97.6 g, 0.4 moles), methylene chloride (600 g), DMAP (0.04 g) and triethylamine (50.4 g, 0.504 moles) and the resulting mixture cooled to 0-5° C. Added dropwise over an hour was methacryloyl chloride (50 g, 0.48 moles). After the addition was complete, the reaction was held at <10° C. for 30 minutes then heated to reflux and held for six hours. GC analysis indicated starting material remained so additional methacryloyl chloride (6 g) and triethylamine (6 g) were added. After one hour at reflux, the reaction was cooled and 600 mL demineralized water added. Lower product layer decanted and upper water layer discarded. Water wash was repeated four times. Organic layer dried with sodium sulfate and then removed with a rotary evaporator to provide 123 g crude product (93.7% GC assay). Material distilled in a Kugelrohr apparatus to provide the desired product in 96% GC assay and 94.9% NMR assay.

Comparative Example 1

Acetoacetoxyethyl Methacrylate (AAEM)

AAEM available from Eastman Chemical Company was used as a control in Comparative Example 1.

Example 3

Accelerated Hydrolysis Testing of Monomers

The predominant mode of decomposition for 1,3-diketo species is loss of the acetoacetyl group via formation of acetone and carbon dioxide as shown in Equation 1.

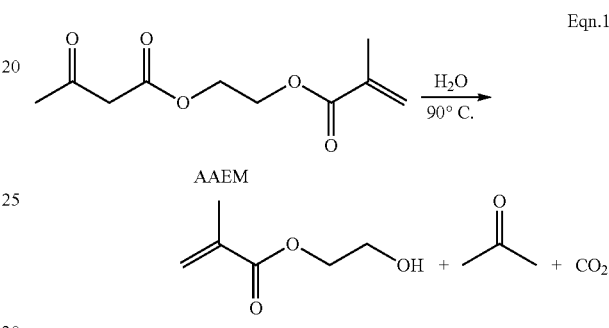

It is possible to monitor this decomposition by either HPLC analysis of the starting materials and decomposition products (AAEM and HEMA in Eqn. 1) or by GC analysis of the acetone.

To evaluate the monomers in a reasonable length of time, an accelerated hydrolysis test was used to evaluate the hydrolytic stability of the new molecules. A solution of 0.5% of the monomer in water was held at 90° C. and samples analyzed by HPLC over time. The disappearance of the starting monomer and the concurrent appearance of hydrolysis products can thus be determined and related to the hydrolytic stability of the molecule. In general, the less decomposition seen, the more hydrolytically stable the monomer is.

TABLE 1

Accelerated Hydrolysis Testing of Monomers

| | % Monomer Remaining | |
| --- | --- | --- |
| Time (hr) | Example 1 | Comparative Example 1 |
| 0 | 100.0 | 97.7 |
| 1 | 99.4 | 96.1 |
| 2 | 98.7 | 94.1 |
| 3 | 98.1 | 91.4 |
| 5 | 96.9 | 85.0 |
| 8 | | 77.9 |
| 24 | 91.4 | 43.2 |
| 30 | | 35.1 |
| 48 | 88.1 | 9.8 |
| 54 | | 7.8 |
| 120 | 78.8 | |

As demonstrated in Table 1, the novel substituted 3-oxopentanoate of Example 1 was remarkably more hydrolytically stable than AAEM (Comparative Example 1).

Example 4

Demonstration of Self-Initiating UV Cure

Films (3 mil wet) of Example 1 and Comparative Example 1 monomers were drawn down on glass slides and passed through an American Ultraviolet Co.—Min-Lab UV Curing Machine (CTL 00035; medium pressure Hg lamp; 300 WPI; 20 FPM; 576 mJ/cm$^2$—avg. of 3 tests with UVPS Compact Radiometer) multiple times. The results are shown in Table 2 and demonstrate that the novel compounds exemplified by Example 1 are able to self-initiate and cure under exposure to UV light. The Comparative Example, AAEM, did not cure under similar conditions.

TABLE 2

| Self-Initiating UV Cure. | |
| --- | --- |
| | UV Curing Results |
| Example 1 | Clear, solid film |
| Comparative Example 1 | Liquid |

Example 5

Preparation of Solution Acrylic Containing Monomer of Example 1

A 500 mL resin kettle equipped with a heating mantle, air-driven agitator, nitrogen blanket, thermocouple, temperature controller, condenser, pump and balance was charged with ethyl 3-ethoxypropionate (EEP, 118.33 g) and heated to 100° C. Methyl methacrylate (90.69 g), butyl acrylate (93.74 g), Example 1 monomer (78.15 g) and Vazo 67 initiator were mixed and placed in a suitable container. Using a pump, the monomer mixture was added to the heated solvent over five hours at approximately 1 g/min. After the addition was complete, the reaction was held at 100° C. for 30 minutes and then a post-add solution of Vazo 67 (1.85 g) in EEP (16.67 g) was pumped in to terminate the reaction. The resulting solution was cooled and bottled. Analysis of the resulting resin gave the following:

$T_g$: 10.44° C. (midpoint of $2^{nd}$ heat)
MW: $M_w$—26498, $M_n$—10035, $M_w/M_n$=2.64
Brookfield Viscosity: 6059 cP @20 RPM
Color: 0.4 Gardner; 74 APHA

Comparative Example 2

Preparation of Solution Acrylic Containing AAEM

Same procedure used as in Example 5 except acetoacetoxyethyl methacrylate (AAEM) was used. Analysis of the resulting resin gave the following:

$T_g$: 8.59° C. (midpoint of $2^{nd}$ heat)
MW: $M_w$—23417, $M_n$—9526, $M_w/M_n$=2.46
Brookfield Viscosity: 9718 cP @20 RPM
Color: 0.2 Gardner; 49 APHA

Example 6

Demonstration of Self-Initiated UV Cure of Solution Acrylics

Samples of the Example 5 resin and the Comparative Example 2 resin in glass vials were placed in a UV light box (6 UVA-340 light bulbs (Q-Panel Co.) at a height of 5 inches from sample—4.8 J/cm$^2$/hr (avg. of three 5-minute tests with UVPS Compact Radiometer)). After 15 hours exposure, the Example 5 resin was a solid gel and would not flow indicating cross-linking had occurred. In contrast, the Comparative Example 2 resin remained a fluid and flowed easily indicating that no cross-linking occurred.

Example 7

UV Cure of Solution Acrylics

Films (3 mil wet) of Example 5 and Comparative Example 2 solution acrylics were evaluated by drawing them down on glass slides and subjecting them to various treatments. The films were either (1) baked at 90° C. for 1 hour or (2) baked at 90° C. for 1 hour and then passed through an American Ultraviolet Co.—Min-Lab UV Curing Machine (CTL 00035; medium pressure Hg lamp; 300 WPI; 20 FPM; 576 mJ/cm$^2$—avg. of 3 tests with UVPS Compact Radiometer) multiple times or (3) passed through the UV curing machine multiple times and then baked at 90° C. for 1 hour or finally, (4) placed in a UV light box (6 UVA-340 light bulbs (Q-Panel Co.) at a height of 5 inches from sample—4.8 J/cm$^2$/hr (avg. of three 5-minute tests with UVPS Compact Radiometer)) and then baked at 90° C. for 1 hour. The baking at 90° C. for 1 hour was necessary to remove any remaining traces of EEP. The results of these evaluations are contained in Table 3.

TABLE 3

| Self-Initiated UV Cure of Solution Acrylics. | | | | | | | | | | | | | | |
| --- | --- | --- | --- | --- | --- | --- | --- | --- | --- | --- | --- | --- | --- | --- |
| Example 5 Solution Acrylic | 100 | | 100 | | 100 | | 100 | | 70 | | 70 | | 70 | |
| Comparative Example 2 Solution Acrylic | | 100 | | 100 | | 100 | | 100 | | 70 | | 70 | | 70 |
| Trimethylolpropane triacrylate (TMPTA) | | | | | | | | | 30 | 30 | 30 | 30 | 30 | 30 |
| Konig Pendulum Hardness (sec)[1] | | | | | | | | | | | | | | |
| baked @ 90° C./1 hour | 19 | 15 | | | | | | | | | | | | |
| baked @ 90° C./1 hour then UV processor - 32 passes | | | 21 | 18 | | | | | tacky | tacky | | | | |
| | | | | | 38 | 24 | | | | | 103 | 96 | | |
| UV processor - 32 passes then baked @ 90° C./1 hr | | | | | | | tacky | tacky | | | | | 40 | 33 |
| | | | | | | | 50 | 26 | | | | | 103 | 62 |

TABLE 3-continued

Self-Initiated UV Cure of Solution Acrylics.

| | | | | | | | | | | | | | | |
|---|---|---|---|---|---|---|---|---|---|---|---|---|---|---|
| 15 hours UV light box | | | | | | 23 | 19 | | | | | 29 | | tacky |
| 87 hours UV light box | | | | | | 50 | 36 | | | | | 99 | | 43 |
| then baked @ 90° C./1 hr | | | | | | 88 | 52 | | | | | 121 | | 53 |

$T_g$ (° C.) of final dried film

| | | | | | | | | | | | | | | |
|---|---|---|---|---|---|---|---|---|---|---|---|---|---|---|
| 10 | 9 | 16 | 13 | 18 | 11 | 23 | 19 | 29 | 24 | 24 | 14 | 29 | | 17 |

[1]Average of three tests.

The higher Konig Hardness and Tg shown in the Example 5 films demonstrates the improvement created by the self-initiated UV cross-linking and curing.

Water-Based Latexes

In general, a water-based latex of the invention may be prepared by polymerizing acrylic (ethylenically unsaturated) monomers in the presence of substituted 3-oxopentanoate monomer of the invention. Before conducting polymerization, these ethylenically unsaturated monomers are either pre-emulsified in water/surfactant mixture or used as such.

The polymerization process of making these 'acrylic' latexes may also require an initiator (oxidant), a reducing agent, or a catalyst. Suitable initiators include conventional initiators such as ammonium persulfate, sodium persulfate, hydrogen peroxide, t-butyl hydroperoxide, ammonium or alkali sulfate, di-benzoyl peroxide, lauryl peroxide, di-tertiarybutylperoxide, 2,2-azobisisobutyronitrile, benzoyl peroxide, and the like.

Suitable reducing agents are those which increase the rate of polymerization and include, for example, sodium bisulfite, sodium hydrosulfite, sodium formaldehyde sulfoxylate, ascorbic acid, isoascorbic acid, and mixtures thereof.

Suitable catalysts are those compounds which promote decomposition of the polymerization initiator under the polymerization reaction conditions thereby increasing the rate of polymerization. Suitable catalysts include transition metal compounds and driers. Examples of such catalysts include, but are not limited to, AQUACAT™, ferrous sulfate heptahydrate, ferrous chloride, cupric sulfate, cupric chloride, cobalt acetate, cobaltous sulfate, and mixtures thereof.

A conventional surfactant or a combination of surfactants is used as a stabilizer, such as an anionic or non-ionic emulsifier, in the suspension or emulsion polymerization preparation of a latex of the invention. Examples of preferred surfactants include, but are not limited to, alkali or ammonium alkylsulfate, alkylsulfonic acid, or fatty acid, oxyethylated alkyphenol, sulfosuccinates and derivatives, or any combination of anionic or non-ionic surfactants. A list of suitable surfactants is available in the treatise: McCutcheon's Emulsifiers & Detergents, North American Edition, MC Publishing Co., Glen Rock, N.J., 1997. Preferably, the surfactant will provide droplet/particle stability, but result in minimal aqueous phase nucleation (micellar or homogeneous).

Example 8

Preparation of a Latex Containing 5 wt. % Example 1 Monomer

To a 1000 ml resin kettle equipped with a condenser, nitrogen purge, and a subsurface feed tube were added 120 g of water and 26 g of 42 nm acrylic latex seed. A nitrogen purge was begun and the contents were stirred and heated to 85° C. Monomers pre-emulsion was prepared by mixing 135 g of water, 7 g of Dowfax 2A1 surfactant and 300 g of acrylic monomers consisting of methylmethacrylate/n-butyl acrylate/acrylic acid/Example 1 monomer in weight ratio of 43.0/50.0/2.0/5.0. Initiator feed consisted of 22.0 g of water, 1.3 g of ammonium persulfate and 0.7 g of ammonium carbonate. A kicker solution comprising of 5.0 g of water, 0.4 g of ammonium persulfate was charged to the reactor at 85 C. Immediately, both monomer pre-emulsion and initiator feeds were started simultaneously. Monomer pre-emulsion was fed over 200 minutes and initiator feed was finished at 210 minutes. After the feeds ended, the reactor was held at 85° C. for 60 minutes, before cooling to 60° C. Then 1.5 g of 1% iron sulfate heptahydrate solution was added to the reactor. A reductant solution consisting of 6.0 g water, 0.3 g isoascorbic acid and 0.2 g of 28% ammonium hydroxide along with an initiator solution consisting of 6.0 g water and 0.5 g of 70% t-butyl hydroperoxide were then fed over 30 minutes. After the feeds ended, the reaction mixture was held for additional 30 minutes and then cooled to room temperature. The latex was filtered through a 100 mesh wire screen to filter any solids or scrap. The droplet and particle sizes were measured using Mictrotrac UPA laser light-scattering device (180 degree backscattering). The droplets and particles were diluted approximately 1:50 in water for particle size measurement. Resulting latex had the following properties:

Solids: 49.60%; PS 143 nm
$T_g$: 13.24° C. (midpoint of $2^{nd}$ heat)
MW: $M_w$—242628, $M_n$—29245, $M_w/M_n$=8.3

Example 9

Preparation of Latex Containing 10 wt. % Example 1 Monomer

Same procedure as Example 8 except monomers pre-emulsion was prepared by mixing 135 g of water, 7 g of Dowfax 2A1 surfactant and 300 g of acrylic monomers consisting of methylmethacrylate/n-butyl acrylate/acrylic acid/Example 1 monomer in ratio of 40.0/48.0/2.0/10.0. Resulting latex had the following properties:

Solids: 49.80%; PS 145 nm
$T_g$: 14.20° C. (midpoint of $2^{nd}$ heat)
MW: $M_w$—168866, $M_n$—23394, $M_w/M_n$=7.2

Comparative Example 3

Preparation of Latex Containing 10% AAEM

Same procedure as Example 8 except monomers pre-emulsion was prepared by mixing 135 g of water, 7 g of Dowfax 2A1 surfactant and 300 g of acrylic monomers consisting of methylmethacrylate/n-butyl acrylate/acrylic acid/AAEM in ratio of 40.0/48.0/2.0/10.0. Resulting latex had the following properties:

Solids: 49.89%; PS 146 nm
$T_g$: 15.59° C. (midpoint of $2^{nd}$ heat)
MW: $M_w$—143092, $M_n$—30596, $M_w/M_n$=4.7

Comparative Example 4

Preparation of Control Acrylic Latex

Same procedure as Example 8 except monomers pre-emulsion was prepared by mixing 135 g of water, 7 g of Dowfax 2A1 surfactant and 300 g of acrylic monomers consisting of methylmethacrylate/n-butyl acrylate/acrylic acid in ratio of 46.0/52.0/2.0. Resulting latex had the following properties:
Solids: 49.50%; PS 148 nm
$T_g$: 14.41° C. (midpoint of $2^{nd}$ heat)
MW: $M_w$—182908, $M_n$—31481, $M_w/M_n$=5.8

Example 10

Comparison of 5% and 10% Example 1 Monomer Latexes in Dark and UVA Exposure

Films (3 mil wet) of Example 8 and Example 9 latexes were evaluated by drawing them down on glass slides and subjecting them to various treatments. The films were either (1) air dried at room temperature or (2) air dried at room temperature and then placed in a UV light box (6 UVA-340 light bulbs (Q-Panel Co.) at a height of 5 inches from sample—4.8 $J/cm^2$/hr (avg. of three 5-minute tests with UVPS Compact Radiometer)). The results of these evaluations are contained in Table 4.

TABLE 4

Self Initiated UV Cure of Latexes.

| | Konig Pendulum Hardness (sec)[1] | | | | | |
|---|---|---|---|---|---|---|
| | Example 8 Latex | | | Example 9 Latex | | |
| Time (hrs) | Air Dry | UV Light Box | UV Light Box/ Air Dry | Air Dry | UV Light Box | UV Light Box/ Air Dry |
| 0.5 | 24 | 24 | 1.0 | 18 | 18 | 1.0 |
| 16 | 24 | 25 | 1.0 | 27 | 29 | 1.0 |
| 96 | 32 | 39 | 1.2 | 36 | 59 | 1.6 |
| 144 | 24 | 32 | 1.3 | 28 | 52 | 1.9 |
| 264 | 28 | 45 | 1.6 | 34 | 65 | 1.9 |
| 360 | 26 | 41 | 1.6 | 30 | 66 | 2.2 |
| 432 | 33 | 55 | 1.7 | 38 | 81 | 2.1 |
| $T_g$ (° C.) of final dried film | | | | | | |
| | 13 | 16 | 1.2 | 14 | 21 | 1.5 |

[1]Average of three tests.

The increase in Konig Hardness and Tg between the 5% Example 8 and 10% Example 9 films demonstrate the improvement created by the self-initiated UV cross-linking and curing provided by the novel monomers of the invention.

Example 11

Comparison of 10% Example 1 Monomer, 10% AAEM and Acrylic Control in Air Dry and UVA Exposure Films (3 mil wet) of Example 9, Comparative Example 3 and Comparative Example 4 latexes were evaluated by drawing them down on glass slides and subjecting them to various treatments. The films were either (1) air dried at room temperature or (2) air dried at room temperature and then placed in a UV light box (6 UVA-340 light bulbs (Q-Panel Co.) at a height of 5 inches from sample—8.0 $J/cm^2$/hr (avg. of three 5-minute tests with UVPS Compact Radiometer)). The results of these evaluations are contained in Table 5.

TABLE 5

Self Initiated UV Cure of Latexes.

| | Konig Pendulum Hardness (sec)[1] | | | | | | | | |
|---|---|---|---|---|---|---|---|---|---|
| | Example 9 Latex | | | Comparative Example 3 Latex | | | Comparative Example 4 Latex | | |
| Time (wks) | Air Dry | UV Light Box | UV Light Box/ Air Dry | Air Dry | UV Light Box | UV Light Box/ Air Dry | Air Dry | UV Light Box | UV Light Box/ Air Dry |
| 1 | 29 | 54 | 1.9 | 31 | 76 | 2.5 | 28 | 28 | 1.0 |
| 3 | 28 | 71 | 2.5 | 29 | 79 | 2.7 | 35 | 37 | 1.1 |
| 6 | 37 | 100 | 2.7 | 39 | 114 | 2.9 | 57 | 64 | 1.1 |
| $T_g$ (° C.) of final dried film | | | | | | | | | |
| | 15 | 26 | 1.7 | 14 | 27 | 1.9 | 18 | 17 | 0.9 |

[1]Average of three tests.

The increase in Konig Hardness and Tg demonstrated by the Example 9 Latex is much better than the acrylic control latex (Comparative Example 4) and is comparable to the AAEM latex (Comparative Example 3). This improvement in film properties coupled with the improvement in hydrolytic stability demonstrates the utility of this class of novel monomers.

Example 12

Evaluation of Examples 1 and 2 as Coalescents

Coalescent performance was determined in two latex systems: Rhoplex SG-30, an acrylic latex available from Rohm & Haas; and Rhoplex HG-74, a styrene-acrylic latex also available from Rohm & Haas. Samples were prepared at two coalescent concentrations: 5 phr and 10 phr. After adding the calculated amount of coalescent dropwise to each latex emulsion with stirring, the samples were stirred for an additional 30 minutes on the magnetic stirrer. The samples were then transferred into 8 dram vials and allowed to further equilibrate by rolling overnight (or longer) at ambient lab temperature using standard lab rollers. The samples were then drawn down on the MFFT bar and allowed to dry. The MFFT values were determined by locating the position on each film where cracking stopped and converting that position to degrees Fahrenheit using the calibration chart for that instrument. The MFFT results are summarized in Table 6. MFFT results for Texanol ester alcohol and Optifilm Enhancer 400, two widely used coalescents from Eastman, are also reported in Table 6 for comparison purposes.

TABLE 6

MFFT Comparison.

| Coalescent | Latex | phr | MFFT (° F.) | Comments |
|---|---|---|---|---|
| Example 1 | Rhoplex SG-30 | 5 | 39.2 | heterogeneous liquid, clear film |
| | | 10 | <32.0 | heterogeneous liquid, clear film |
| | Rhoplex HG-74 | 5 | 53.6 | heterogeneous liquid, clear film |
| | | 10 | <32.0 | heterogeneous liquid, clear film |
| Example 2 | Rhoplex SG-30 | 5 | 39.3 | homogeneous liquid, clear film |
| | | 10 | <32.0 | homogeneous liquid, clear film |
| | Rhoplex HG-74 | 5 | 55.5 | slight pink, homogeneous liquid, clear film |
| | | 10 | 37.4 | pink tint, homogeneous liquid, clear film |
| Texanol Ester Alcohol | Rhoplex SG-30 | 5 | 34.8 | clear films, homogeneous liquid |
| | | 10 | <32.0 | clear films, homogeneous liquid |
| | Rhoplex HG-74 | 5 | 52.8 | clear films, homogeneous liquid |
| | | 10 | 32.8 | clear films, homogeneous liquid |
| Optifilm Enhancer 400 | Rhoplex SG-30 | 5 | 39.4 | clear films, homogeneous liquid |
| | | 10 | 34.3 | clear films, homogeneous liquid |
| | Rhoplex HG-74 | 5 | 44 | film very slight haze, homogeneous liquid |
| | | 10 | <32.0 | film very slight haze, homogeneous liquid |

In general, an MFFT value of less than 40° F. in Rhoplex SG-30 at a coalescent concentration of 5 phr equates to a good performing coalescent. The lower the MFFT, the more efficient the coalescent. At a concentration of 10 phr in this latex, the film formation temperature is typically well below 32° F., the lower detection limit of the machine under standard operating conditions. With the higher Tg HG-74 polymer, the observed MFFT is not as low as that observed in SG-30. At 5 phr, a MFFT value of less than 55° F. indicates good coalescent efficiency whereas a value of less than 50° F. is especially noteworthy. At 10 phr in HG-74, the MFFT of efficient coalescents is typically at or below 32° F.

Based on these criteria, both Example 1 and Example 2 performed well as coalescents in the two latex emulsions used in this study. Coalescent efficiency was essentially identical in the SG-30 latex whereas Example 1 appeared to be slightly more efficient than Example 2 in the HG-74 latex. In addition, the performance of these two materials was comparable to the two controls (Texanol and Optifilm Enhancer 400).

Example 13

Evaluation of Examples 1 and 2 as Reactive Coalescents

For this study, two latex emulsions were used: Rhoplex HG-74 and Rhoplex SG-10. Samples were prepared by charging the calculated amount of each experimental coalescent dropwise with stirring to 45.0 grams of the latex emulsion in 2.5 ounce jars to yield a coalescent concentration of 10 phr. The resulting mixtures were stirred for an additional 2 hours to ensure good mixing then rolled for 10 days to fully equilibrate the coalescent in the latex emulsion. Drawdowns (4 mil wet thickness) were made on tared glass plates (3"×8") and allowed to air-dry for 4 days. The plates were reweighed to determine the initial film weight. Tukon hardness and König hardness were determined on dried films from each coalescent/latex combination. This data was used to establish the hardness of the films prior to UV or heat exposure. Half the remaining plates were placed in a QUV cabinet equipped with UVA 340 bulbs while the other half were stored in a dark oven set at approximately the same temperature as the QUV cabinet (i.e., 50° C.). Thus the only intended difference between plates stored in the QUV cabinet and plates stored in the oven was the exposure to UV radiation. After 7 days, designated plates were removed from the QUV cabinet and from the oven. After equilibrating to room temperature, the plates were reweighed to determine weight loss. In addition, Tukon hardness and König hardness were determined on each film. After 14 days, the process was repeated on the remaining plates. The results are summarized in Table 7.

TABLE 7

Reactive Coalescent Comparison

| | QUV Cabinet | | | 50° C. Oven | | |
|---|---|---|---|---|---|---|
| Sample Exposure (days) | Plate Weight Loss | Tukon Hardness (HK units) | König Hardness (sec) | Plate Weight Loss | Tukon Hardness (HK units) | König Hardness (sec) |
| HG-74 with 10 phr Example 1 | | | | | | |
| 0 | — | 0.9 | 39 | — | 0.9 | 39 |
| 7 | 6.3% | 5.1 | 87 | 6.8% | 4.6 | 107 |
| 14 | 8.0% | 7.6 | 144 | 8.2% | 4.6 | 116 |
| HG-74 with 10 phr Example 2 | | | | | | |
| 0 | — | 0.8 | 36 | — | 0.8 | 36 |
| 7 | 5.7% | 6.0 | 131 | 8.0% | 4.9 | 118 |
| 14 | 7.5% | 7.5 | 147 | 9.1% | 5.3 | 117 |
| SG-10 with 10 phr Example 1 | | | | | | |
| 0 | — | 0.3 | 17 | — | 0.3 | 17 |
| 7 | 5.4% | 2.4 | 82 | 6.6% | 1.5 | 67 |
| 14 | 6.2% | 3.0 | 95 | 6.9% | 1.6 | 74 |
| SG-10 with 10 phr Example 2 | | | | | | |
| 0 | — | 0.3 | 17 | — | 0.3 | 17 |
| 7 | 5.6% | 1.9 | 74 | 7.2% | 0.9 | 53 |
| 14 | 5.0% | 2.1 | 82 | 8.2% | 1.3 | 64 |

Prior to exposure to UV, there does not appear to be any significant difference between the initial hardness measurements of the films containing Example 1 as coalescent versus those containing Example 2, within the same latex type. However it is obvious from the Tukon hardness and Konig hardness data that the films obtained from the SG-10 latex are softer than the films obtained from the HG-74 latex.

After exposure of the films to either UV radiation or just heat alone all films observed a loss in weight with a corresponding increase in hardness. For the plates stored in the 50° C. oven, the weight loss is most likely the result of evaporation of the volatile coalescent from the polymer film. As the coalescent evaporates, the plasticizing effect of the coalescent on the polymer is reduced which corresponds to the observed increase in hardness.

For the films exposed to UV radiation the observed weight loss was consistently less than corresponding films stored in the 50° C. oven for the same period of time. At first glance this could imply the films were actually exposed to hotter conditions in the oven than in the QUV cabinet resulting in higher levels of evaporation of the volatile coalescent. However, if this was the case, the films that experienced the higher weight loss (i.e., those films stored in the oven) would be expected to be harder than the films exposed to the UV radiation. This was not the case. In essentially every case, the films exposed to UV radiation produced harder films than similar films stored in the oven for the same period of time. Therefore a certain percentage of the Example 1 and Example 2 present in the film likely participates in a polymerization reaction and/or cross-linking type of mechanism resulting in the harder films observed in this study.

We claim:

1. A substituted 3-oxopentanoate corresponding to the following formula 1:

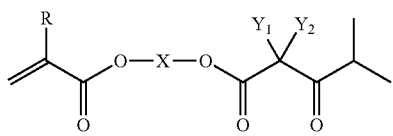
(1)

in which R is hydrogen, or a methyl group;

X is a straight-chain, branched, or cyclic alkyl or alkyl ether group having from 1 to 15 carbon atoms or aromatic group having from 6 to 15 carbon atoms; and Y1 and Y2 are each methyl groups.

2. The substituted 3-oxopentanoate of claim 1, wherein X comprises a branched or straight chain alkyl or alkyl ether group having from 1 to 8 carbon atoms.

3. The substituted 3-oxopentanoate of claim 1, wherein X comprises a cyclic alkyl or alkyl ether group having from 6 to 8 carbon atoms.

4. The substituted 3-oxopentanoate of claim 1, wherein X comprises an aromatic group having from 6 to 15 carbon atoms.

5. The substituted 3-oxopentanoate of claim 1, wherein X has one of the following structures:

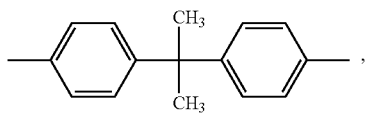
(4)

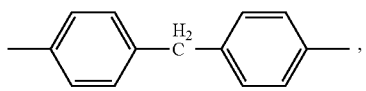
(5)

(6)

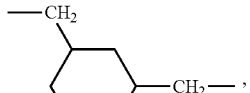
(7)

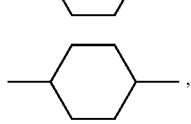
(8)

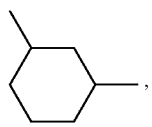
(9)

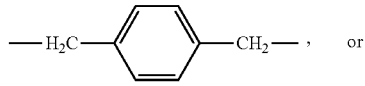
(10)

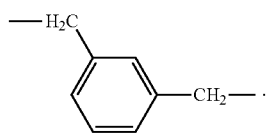
(11)

6. The substituted 3-oxopentanoate of claim 1, wherein X is an alkyl or alkyl ether group having 2 to 6 carbon atoms.

7. The substituted 3-oxopentanoate of claim 1, wherein the molecule corresponds to the following structure:

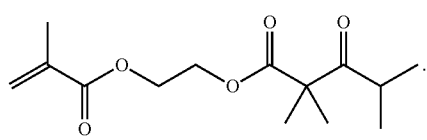
(2)

8. The substituted 3-oxopentanoate of claim 1, wherein the molecule corresponds to the following structure:

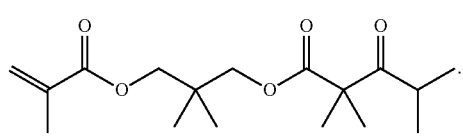
(3)

9. An emulsion polymer comprising residues from the substituted 3-oxopentanoate of claim 1 and one or more additional ethylenically unsaturated monomers.

10. A solution polymer comprising residues from the substituted 3-oxopentanoate monomer of claim 1.

11. The emulsion polymer of claim 10, wherein the one or more additional ethylenically unsaturated monomers comprise one or more of: methyl (meth)acrylate, ethyl (meth)acrylate, propyl (meth)acrylate, isopropyl (meth)acrylate, butyl (meth)acrylate, isobutyl (meth)acrylate, hexyl (meth)acrylate, isooctyl (meth)acrylate, isodecyl (meth)acrylate, lauryl (meth)acrylate, stearyl (meth)acrylate, phenoxyethyl (meth)acrylate, methoxyethyl (meth)acrylate, benzyl (meth)acrylate, ethoxyethyl (meth)acrylate, 2-ethylhexyl (meth)acrylate, cyclopentyl (meth)acrylate, isobutyl (meth)acrylate, styrene, p-methyl styrene, o-methyl styrene, p-butyl styrene, or alpha-methyl styrene.

12. A coating composition comprising the substituted 3-oxopentanoate of claim 1, and optionally, one or more additional ethylenically unsaturated monomers.

13. A latex formulation comprising a polymer having residues from the substituted 3-oxopentanoate monomer of claim 1 dispersed in an aqueous carrier.

14. A coating composition comprising a latex emulsion polymer, and the substituted 3-oxopentanoate of claim 1 provided as a coalescent.

* * * * *